United States Patent [19]

Büchel et al.

[11] Patent Number: 4,472,421
[45] Date of Patent: Sep. 18, 1984

[54] **AZOLE ANTIMYCOTICS AND THEIR USE IN TREATING SKIN CONDITIONS CAUSED BY *PITYROSPORUM OVALE***

[75] Inventors: Karl H. Büchel, Burscheid; Manfred Plempel, Haan, both of Fed. Rep. of Germany

[73] Assignee: Bayer Aktiengesellschaft, Fed. Rep. of Germany

[21] Appl. No.: 135,985

[22] Filed: Mar. 31, 1980

Related U.S. Application Data

[63] Continuation of Ser. No. 585,847, Jun. 11, 1975, abandoned.

[30] Foreign Application Priority Data

Jun. 22, 1974 [DE] Fed. Rep. of Germany ....... 2430039

[51] Int. Cl.$^3$ ........................................... A61K 31/415
[52] U.S. Cl. .................................................. 424/273 R
[58] Field of Search .................................... 424/273 R

[56] References Cited

U.S. PATENT DOCUMENTS

| | | | |
|---|---|---|---|
| 2,901,399 | 1/1963 | Neuman | 424/DIG. 4 |
| 3,812,142 | 7/1974 | Meiser et al. | 424/273 X |
| 3,849,548 | 11/1974 | Grand | 424/70 |
| 3,903,287 | 9/1975 | Meiser et al. | 424/273 |
| 4,000,299 | 12/1976 | Kramer | 424/273 |

FOREIGN PATENT DOCUMENTS 2105490  8/1972  Fed. Rep. of Germany ...... 424/273

OTHER PUBLICATIONS

Lubowe, J. of the Soc. Cos. Chem., vol. 12, Jun. 1961, pp. 253–258.
Amer. Perf. & Cos., vol. 78, Oct. 1963, pp. 66–67.
Caspers, Canad M.A.J., Jul. 15, 1958, vol. 79, pp. 113–118.
Roia, J. Soc. Cos. Chem., vol. 14, 1963, pp. 81–88.
Vanderwyk, J. Soc. Cos. Chem., vol. 18, 1967, pp. 629–639.
Gots, Arzneim-Forsch, 2, vol. 21, 1971, pp. 256–257.
Lennette, Man. Clin. Microbiol., ASM, 2nd ed., 1974, pp. 491–505.

*Primary Examiner*—Leonard Schenkman
*Attorney, Agent, or Firm*—Jacobs & Jacobs

[57] ABSTRACT

Compositions are prepared which are useful for treating skin conditions caused, in whole or in part, by *Pityrosporum ovale* which comprise a therapeutically-effective amount of an azole antimycotic in combination with a diluent or carrier suitable for application to human skin.

6 Claims, No Drawings

AZOLE ANTIMYCOTICS AND THEIR USE IN TREATING SKIN CONDITIONS CAUSED BY *PITYROSPORUM OVALE*

CROSS-REFERENCE

This is a continuation of Ser. No. 585,847 filed June 11, 1975, now abandoned.

The present invention relates to compositions containing azole antimycotics and the use thereof, particularly in the treatment of skin conditions caused in whole or in part by *Pityrosporum ovale*.

The use of azole derivatives as medicaments is already known. (See, inter alia, Belgian Pat. No. 720,801, Belgian Pat. No. 741,310, U.S. Pat. No. 3,737,548, German Offenlegungsschrift No. 1,911,646, Belgian Pat. No. 750,724, German Offenlegungsschrift No. 2,016,839, German Offenlegungsschrift No. 2,044,621, German Offenlegungsschrift No. 2,053,080, Belgian Pat. No. 778,973, Belgian Pat. No. 804,092 and *Arzneimittelforschung* 2, Volume 21, 1971, pages 256–257.)

Pyridone derivatives, such as 1-hydroxy-2-pyridones, are known to be useful as anti-dandruff agents and salicylic acid derivatives, such as the 2-ethyl-1,3-hexanediol ester of salicylic acid, are known for combating dandruff and seborrhoea. (See German Offenlegungsschrift No. 2,234,009 and U.S. Pat. No. 2,523,867.)

An itch-suppressant action in seborrhoeic conditions has been described for crotonyl-N-ethyl-o-toluidine. (See O. Saipt, *Wiener MEd. Wschr.*, 102, 413 (1952).)

F. Asbeck has reported on combating microsporiosis with triphenyl-dodecylphosphonium bromide. (See *Z. Haut-und Geschlechtskrankheiten*, 14, 117 (1956).)

It is also known that colloidal sulphur is effective in cases of seborrhoea, dandruff, acne and infections. (See A. J. Wojwod, *J. Gen. Microbiol.*, 10, 509 (1954).)

The preparations comprising colloidal sulphur necessarily contain polythionic acids which have been shown by clinical tests to be effective in cases of seborrhoea and acne. (See J. R. Delaney et al., *J. Michigan St. Med. Soc.*, 50, 1236 (1951).) However, the great instability of the polythionates is a disadvantage.

The effect of various agents against *Pityrosporum ovale*, a blastomycete, which is regarded as one of the principal causes of pathological changes in the skin, especially in the scalp, is not always satisfactory, and, in many cases, agents known in the art have little or no effect.

According to the present invention, it is been discovered that various azole compounds which are known in the art to exhibit antimycotic activity also show marked and substantial activity against the skin changes which are caused in whole or in part by *Pityrosporum ovale*. Thus, the present invention is drawn to compositions which comprise a therapeutically-effective amount of an azole antimycotic in combination with a diluent or carrier which is suitable for application to the skin of a human for the treatment of skin conditions caused, in whole or in part, by *Pityrosporum ovale*.

The basic skeleton of the azole compounds used in the invention consists of a central carbon atom with an optionally substituted azole radical which is preferably imidazole or a triazole. The remaining substituents on the carbon atom are preferably: optionally-substituted phenyl, it being possible for two phenyl rings to be linked to one another (for example, via —(CH$_2$)$_n$—, —CH=CH—, O or S, resulting, for example, in fluorene, dibenzocycloheptane or (thio)-xanthene derivatives); five-membered or six-membered, optionally-substituted hetero-cycles having 1 or 2 N, O or S heteroatoms; aliphatic, acyclic or alicyclic radicals; or functional groups, such as, for example, ester, ether, alkenyl, alkinyl, keto, hydroxyl, amido or amino groups.

According to a preferred embodiment of the present invention, said azole antimycotic is of the formula:

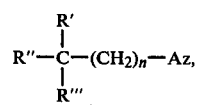

or a physiologically-acceptable, nontoxic salt thereof, wherein

Az is imidazole or a triazole unsubstituted or substituted by alkyl of 1 to 4 carbon atoms;

R', R'' and R''' are each selected from the group consisting of hydrogen, unsubstituted or substituted phenyl, an unsubstituted or substituted heterocycle, an unsubstituted or substituted aliphatic moiety, an unsubstituted or substituted alicyclic moiety, an ester, an ether, a keto moiety, a hydroxy moiety, an amido moiety or an amino moiety, or R' and R'' are each unsubstituted or substituted phenyl linked together by a direct bond or linking moiety; and n is 0 or 1.

According to one embodiment of the present invention the azole antimycotic is of the formula

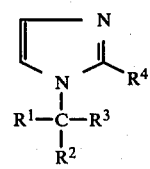

or a physiologically-acceptable, nontoxic salt thereof, wherein $R^1$ is phenyl unsubstituted or substituted by 1 or 2 substituted selected from the group consisting of halogen, alkyl of 1 to 4 carbon atoms, trifluoromethyl, nitro and alkoxy of 1 to 4 carbon atoms;

$R^2$ is phenyl unsubstituted or substituted by halo or nitro; or pyridyl;

$R^3$ is phenyl unsubstituted or substituted by halo; imidazolyl unsubstituted or substituted by alkyl of 1 to 4 carbon atoms; or pyridyl; and $R^4$ is hydrogen or alkyl of 1 to 4 carbon atoms.

According to another embodiment of the present invention $R^1$ is phenyl unsubstituted or substituted by 1 or 2 substituents selected from the group consisting of chloro, bromo, fluoro, alkyl of 1 to 4 carbon atoms, trifluoromethyl, nitro and alkoxy of 1 to 4 carbon atoms;

$R^2$ is phenyl unsubstituted or substituted by chloro, fluoro or nitro; or pyridyl;

$R^3$ is phenyl unsubstituted or substituted by fluoro or chloro; imidazolyl unsubstituted or substituted by alkyl of 1 to 2 carbon atoms; or pyridyl; and $R^4$ is hydrogen or alkyl of 1 to 2 carbon atoms.

According to another embodiment of the present invention the azole antimycotic is of the formula

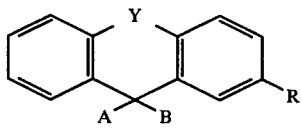

or a physiologically-acceptable, nontoxic salt thereof, wherein

A is phenyl unsubstituted or substituted by halo or thioalkyl of 1 or 2 carbon atoms; pyridyl; alkyl of 1 to 4 carbon atoms; alkenyl of 2 to 4 carbon atoms; or carbalkoxy of 1 to 4 carbon atoms in the alkoxy moiety;

B is imidazolyl or a triazole;

R is hydrogen or halo; and

Y is a direct bond, $(CH_2)_2$, CH=CH, oxygen or sulphur.

According to another embodiment of the present invention

A is phenyl unsubstituted or substituted by chloro, bromo, fluoro or thioalkyl of 1 to 2 carbon atoms; pyridyl; alkyl of 1 to 4 carbon atoms; alkenyl of 2 or 3 carbon atoms; or carbalkoxy of 1 to 4 carbon atoms in the alkoxy moiety;

B is imidazolyl or 1,2,4-triazolyl; and

R is hydrogen or chloro.

According to another embodiment of the present invention the azole antimycotic is of the formula

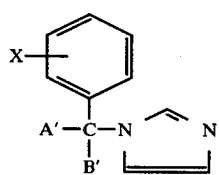

or a physiologically-acceptable, nontoxic salt thereof, wherein

A' is phenyl unsubstituted or substituted by halo or alkyl of 1 to 2 carbon atoms; or pyridyl;

B' is t-butyl, allyl, cycloalkyl of 3 to 6 carbon atoms unsubstituted or substituted by alkyl of 1 or 2 carbon atoms, thienyl, isoxazolyl unsubstituted or substituted by alkyl of 1 or 2 carbon atoms, imidazolyl unsubstituted or substituted by alkyl of 1 or 2 carbon atoms, isothiazolyl unsubstituted or substituted by 1 or 2 halo moieties, piperazinyl or 1,3-diazocyclohexenyl unsubstituted or substituted by 1 to 3 halo moieties; and X is hydrogen or 1 or 2 substituents selected from the group consisting of halo, alkyl of 1 or 2 carbon atoms and trifluoromethyl.

According to another embodiment of the present invention

A' is phenyl unsubstituted or substituted by chloro, fluoro or alkyl of 1 or 2 carbon atoms; or pyridyl;

B' is t-butyl, allyl, cycloalkyl of 5 or 6 carbon atoms unsubstituted or substituted by alkyl of 1 or 2 carbon atoms, thienyl, isoxazolyl unsubstituted or substituted by alkyl of 1 or 2 carbon atoms, imidazolyl unsubstituted or substituted by alkyl of 1 or 2 carbon atoms, isothiazolyl unsubstituted or substituted by 1 or 2 chloro moieties, piperazinyl or 1,3-diazocyclohexenyl unsubstituted or substituted by 1 to 3 chloro moieties; and X is hydrogen or 1 or 2 substituents selected from the group consisting of chloro, fluoro, alkyl of 1 or 2 carbon atoms and trifluoromethyl.

According to another embodiment of the present invention the azole antimycotic is of the formula

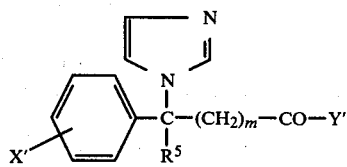

or a physiologically-acceptable, nontoxic salt thereof, wherein $R^5$ is phenyl unsubstituted or substituted by halo, alkyl of 1 to 4 carbon atoms, or alkoxy of 1 or 2 carbon atoms;

X' is hydrogen, halo or alkoxy of 1 or 2 carbon atoms;

Y' is alkoxy of 1 to 12 carbon atoms, lower alkyl, phenyl, mono- or di-alkylamino of 1 or 2 carbon atoms in the alkyl moiety, morpholino or piperazinyl unsubstituted or substituted by alkyl of 1 or 2 carbon atoms; and m is 0 or 1.

According to another embodiment of the present invention $R^5$ is phenyl unsubstituted or substituted by chloro, alkyl of 1 to 4 carbon atoms, or alkoxy of 1 or 2 carbon atoms;

X' is hydrogen, chloro or alkoxy of 1 or 2 carbon atoms;

Y' is alkoxy of 1 to 10 carbon atoms, alkyl of 1 to 4 carbon atoms, phenyl, mono- or di-alkylamino of 1 or 2 carbon atoms in the alkyl moiety, morpholino or piperazinyl unsubstituted or substituted by alkyl of 1 or 2 carbon atoms on a ring nitrogen; and m is 0 or 1.

According to another embodiment of the present invention the azole antimycotic is of the formula

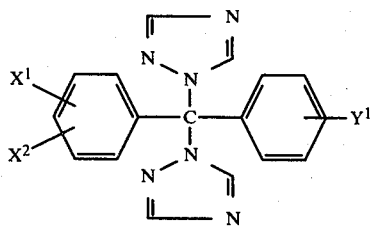

wherein
$X^1$ is hydrogen, halo or nitro;
$X^2$ is hydrogen or halo; and
$Y^1$ is hydrogen or cyano.

According to another embodiment of the present invention
$X^1$ is hydrogen, chloro or nitro;
$X^2$ is hydrogen, chloro or fluoro; and
$Y^1$ is hydrogen or cyano.

According to another embodiment of the present invention the azole antimycotic is of the formula $$\underset{E}{\overset{N}{\underset{\Vert}{\diagdown}}}\underset{}{\overset{}{\underset{}{N}}}-\underset{B^1}{\overset{A^1}{\underset{|}{C}}}-\underset{}{\overset{}{\underset{}{\text{phenyl}}}}-X^3-\text{phenyl}$$

wherein
E is —CH— or N;
$A^1$ is phenyl unsubstituted or substituted by halo; imidazolyl unsubstituted or substituted by alkyl of 1 or 2 carbon atoms; or pyrazolyl unsubstituted or substituted by 1 or 2 alkyl moieties of 1 or 2 carbon atoms;
$B^1$ is phenyl unsubstituted or substituted by halo; and
$X^3$ is a direct bond, oxygen, sulphur or —CO—.

According to another embodiment of the present invention
$A^1$ is phenyl unsubstituted or substituted by chloro; imidazolyl unsubstituted or substituted by alkyl of 1 or 2 carbon atoms; or pyrazolyl unsubstituted or substituted by 1 or 2 alkyl moieties of 1 or 2 carbon atoms; and
$B^1$ is phenyl unsubstituted or substituted by chloro.

According to another embodiment of the present invention the azole antimycotic is of the formula $$X''-\text{phenyl}-\underset{N}{\overset{Y''}{\underset{|}{C}}}-\text{phenyl}-X''$$

or a physiologically-acceptable, nontoxic salt thereof, wherein
X″ is hydrogen or halo; and
Y″ is COO—ALK—Y‴, wherein
ALK is alkylene or alkylidene of 2 to 4 carbon atoms, and
Y‴ is dialkylamino of 1 or 2 carbon atoms or morpholino; or
CO—NH—ALK—Y⁗, wherein
ALK is as above defined, and
Y⁗ is dialkylamino of 1 or 2 carbon atoms in each alkyl moiety.

According to another embodiment of the present invention
X″ is hydrogen or chloro; and
Y″ is COO—CH$_2$—CH$_2$—N(CH$_3$)$_2$;

$$\text{COO}-\underset{|}{\overset{CH_3}{\underset{}{CH}}}-\text{CH}_2-\text{N(CH}_3)_2;$$

CONH—CH$_2$—CH$_2$—CH$_2$—N(C$_2$H$_5$)$_2$; or $$\text{COO}-\underset{|}{\overset{CH_3}{\underset{}{CH}}}-\text{CH}-\text{N}\diagup\!\!\!\diagdown\underset{CH_2-CH_2}{\overset{CH_2-CH_2}{}}\text{O}.$$

According to another embodiment of the present invention the azole antimycotic is of the formula $$R^8-\text{phenyl}-\underset{N}{\overset{X^4}{\underset{|}{C}}}-\underset{R^7}{\overset{R^6}{\underset{|}{C}}}-A^2-Y^2$$

or a physiologically-acceptable, nontoxic salt thereof, wherein
$X^4$ is phenyl or t.-butyl;
$Y^2$ is hydrogen; alkylcarbonyl of 1 to 4 carbon atoms in the alkyl moiety; alkylsulphonyl of 1 to 4 carbon atoms in the alkyl moiety;

$$\text{CH}_3-\text{NH}-\text{CO}-\underset{|}{\overset{}{\underset{CH_3}{N}}}-\text{CO}-;$$

phenyl unsubstituted or substituted by halo; benzoyl unsubstituted or substituted in the ring portion by 1 or 2 substituents selected from the group consisting of halo and nitro; cinnamoyl; or $$\text{CH}_3-\text{phenyl}-\text{SO}_2\text{NH}-\text{CO}-;$$

$R^6$ is hydrogen; halo; alkyl of 1 to 4 carbon atoms or phenyl;
$R^7$ and $R^8$ are each hydrogen; halo or alkyl of 1 to 4 carbon atoms; and
$A^2$ is oxygen, sulphur, —SO$_2$— or —NH—.

According to another embodiment of the present invention
$Y^2$ is hydrogen, alkylcarbonyl of 1 or 2 carbon atoms in the alkyl moiety, alkylsulphonyl of 1 or 2 carbon atoms in the alkyl moiety, $$\text{CH}_3-\text{NH}-\text{CO}-\underset{|}{\overset{}{\underset{CH_3}{N}}}-\text{CO}-,$$

phenyl unsubstituted or substituted by chloro, benzoyl unsubstituted or substituted by chloro or 1 or 2 nitro moieties, cinnamoyl, or

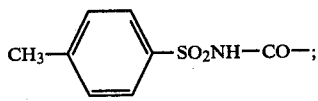

$R^6$ is hydrogen, chloro, alkyl of 1 or 2 carbon atoms or phenyl; and $R^7$ and $R^8$ are each hydrogen, chloro or alkyl of 1 or 2 carbon atoms.

According to another embodiment of the present invention the azole antimycotic is of the formula

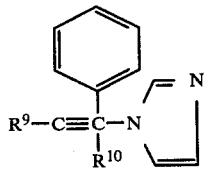

wherein $R^9$ is hydrogen; phenyl; benzyloxy unsubstituted or substituted by alkyl of 1 or 2 carbon atoms; lower alkyl; mono- or di-alkylamino of 1 or 2 carbon atoms in each alkyl moiety; or morpholinoalkyl of 1 or 2 carbon atoms; and $R^{10}$ is phenyl unsubstituted or substituted by alkyl of 1 or 2 carbon atoms, halo or nitro; or alkyl of 1 to 4 carbon atoms.

According to another embodiment of the present invention $R^9$ is hydrogen, phenyl, benzyloxy unsubstituted or substituted by alkyl of 1 or 2 carbon atoms, alkyl of 1 to 5 carbon atoms, mono- or di-(lower alkylamino) of 1 or 2 carbon atoms in each alkyl moiety, or morpholinomethyl; and $R^{10}$ is phenyl unsubstituted or substituted by alkyl of 1 or 2 carbon atoms, chloro or nitro; or alkyl of 1 to 4 carbon atoms.

According to another embodiment of the present invention the azole antimycotic is of the formula

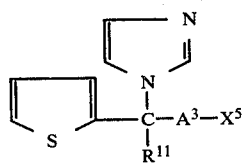

or a physiologically-acceptable, nontoxic salt thereof, wherein $R^{11}$ is phenyl unsubstituted or substituted by halo; or thienyl;

$A^3$ is —CO— or —CH$_2$—; and $X^5$ is alkoxy of 1 to 4 carbon atoms; cyano; —CO—N(alkyl), wherein the alkyl moiety is of 1 to 4 carbon atoms; or —O—ALK'—N(dialkyl), wherein ALK' is alkylene of 2 or 3 carbon atoms or alkylidene of 3 carbon atoms, and the alkyl moieties are each of 1 or 2 carbon atoms.

According to another embodiment of the present invention $R^{11}$ is phenyl unsubstituted or substituted by chloro; or thienyl; and $X^5$ is alkoxy of 1 or 2 carbon atoms, cyano, —CO—N(dialkyl) wherein the alkyl moiety is of 1 to 2 carbon atoms, or —O—ALK'—N(dialkyl), wherein ALK' is alkylidene of 3 carbon atoms and each alkyl moiety is of 1 or 2 carbon atoms.

According to another embodiment of the present invention the azole antimycotic is of the formula

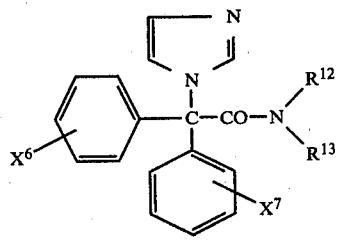

wherein $X^6$ is hydrogen or halo;

$X^7$ is hydrogen or halo;

$R^{12}$ is phenyl unsubstituted or substituted by alkyl of 1 or 2 carbon atoms or trifluoromethyl; or cyclohexyl;

$R^{13}$ is hydrogen or $R^{12}$ and $R^{13}$ form a 6-membered heterocyclic ring together with the nitrogen atom to which they are attached, said heterocycle additionally containing an oxygen, SO$_2$ or nitrogen heteroatom, said heterocycle being unsubstituted or substituted by carb(lower alkoxy) or phenyl.

According to another embodiment of the present invention $X^6$ is hydrogen or chloro;

$X^7$ is hydrogen or chloro;

$R^{12}$ is phenyl unsubstituted or substituted by alkyl of 1 or 2 carbon atoms or trifluoromethyl; or a cyclohexyl;

$R^{13}$ is hydrogen; or $R^{12}$ and $R^{13}$, together with the nitrogen atom to which they are attached, form a 6-membered heterocycle, said heterocycle additionally containing SO$_2$ as a ring member, which heterocycle is either unsubstituted or substituted by phenyl, or said heterocycle containing NH as a ring member whih is either unsubstituted or the hydrogen atom of which is substituted by a carbalkoxy moiety of 1 or 2 carbon atoms in the alkoxy portion.

According to another embodiment of the present invention the azole antimycotic is of the formula

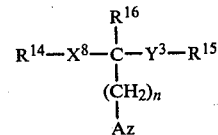

or a physiologically-acceptable, nontoxic salt thereof, wherein

Az is imidazolyl or a triazolyl;

n is 0 or 1;

$X^8$ is oxygen or sulphur;

$Y^3$ is CO, C(OH)$_2$, >C=NOH, CHOH, CCH$_3$OH or C(CH$_2$—C$_6$H$_5$)OH;

$R^{14}$ is phenyl unsubstituted or substituted by 1 or 2 substituents selected from the group consisting of halo, alkyl of 1 to 4 carbon atoms, nitro and phenyl; or by 1 moiety selected from the group consisting of hydroxymethyl-substituted phenyl or dichloro-substituted phenyl; or by 3 to 5 chloro moieties;

$R^{15}$ is phenyl unsubstituted or substituted by halo; t-butyl; or cyclohexyl; and $R^{16}$ is hydrogen, lower alkyl or phenyl.

According to another embodiment of the present invention

Az is imidazolyl or 1,2,4-triazolyl;

$R^{14}$ is phenyl unsubstituted or substituted by 1 or 2 chloro, bromo, fluoro, alkyl of 1 to 4 carbon atoms, nitro or phenyl moieties, or by 1 hydroxymethylphenyl moiety, or by 1 dichlorophenyl moiety, or by 5 chloro moieties;

$R^{15}$ is phenyl unsubstituted or substituted by chloro; t-butyl; or cyclohexyl.

According to another embodiment of the present invention the azole antimycotic is of the formula

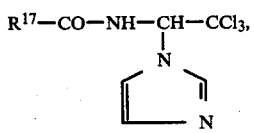

wherein $R^{17}$ is hydrogen, alkyl of 1 to 4 carbon atoms, cyclohexyl or phenyl unsubstituted or substituted by halo.

According to another embodiment of the present invention $R^{17}$ is hydrogen, i-butyl, t-butyl, cyclohexyl or chlorophenyl.

According to another embodiment of the present invention

R', R" and R"' are each selected from the group consisting of hydrogen; phenyl unsubstituted or substituted by 1 or 2 substituents selected from the group consisting of halo, alkyl of 1 to 4 carbon atoms, phenyl and phenoxy; mono- or di-halophenoxy; alkyl of 1 to 4 carbon atoms; alkinyl of 2 to 4 carbon atoms; alkylcarbonyl of 1 to 4 carbon atoms in the alkyl moiety; hydroxy(lower alkyl); carbalkoxy of 1 to 4 carbon atoms in the alkoxy moiety; and imidazolyl; or R' and R" are each phenyl linked to each other by a direct bond or an ethylene bridge;

Az is imidazolyl; and n is 0 or 1.

According to another embodiment of the present invention.

R', R" and R"' are each hydrogen; phenyl unsubstituted by 1 or 2 chloro or bromo moieties, alkyl of 1 or 2 carbon atoms, phenyl, or phenoxy; phenoxy substituted by 1 or 2 chloro or bromo moieties; alkyl of 1 or 2 carbon atoms; alkinyl of 2 or 3 carbon atoms; alkylcarbonyl of 1 to 4 carbon atoms; hydroxy(lower alkyl); or carbalkoxy of 1 to 4 carbon atoms; or R' and R" are each phenyl linked to each other by a direct bond or an ethylene bridge.

The azole antimycotics used as the active agent in the compositions of the present invention are, in part, already known. (See Belgian Pat. No. 720,801, U.S. Pat. No. 3,737,531, Belgian Pat. No. 741,310, U.S. Pat. No. 3,737,548, U.S. Pat. No. 3,711,487, German Offenlegungsschrift No. 1,911,646, Belgian Pat. No. 750,724, German Offenlegungsschrift No. 1,949,012, Belgian Pat. No. 762,463, Belgian Pat. No. 764,700, Belgian Pat. No. 765,585, U.S. Pat. No. 3,732,242, Belgian Pat. No. 770,662, Belgian Pat. No. 771,584, Belgian Pat. No. 772,402, Belgian Pat. No. 774,621, Belgian Pat. No. 776,212, Belgian Pat. No. 778,973, German Offenlegungsschrift No. 2,140,865, Belgian Pat. No. 797,100, Belgian Pat. No. 800,914, Belgian Pat. No. 804,092, Belgian Pat. No. 805,209 and Belgian Pat. No. 805,210.) In part they form the subject of our earlier German Patent application Nos. P 23 244 24 which corresponds to U.S. application Ser. No. 465,617, filed Apr. 30, 1974; P 23 333 55 which corresponds to U.S. application Ser. No. 481,660, filed June 21, 1974; P 23 470 57 which corresponds to U.S. application Ser. No. 504,429, filed Sept. 9, 1974; P 23 501 21 which corresponds to U.S. application Ser. No. 508,684, filed Sept. 23, 1974; P 23 501 24 which corresponds to U.S. application Ser. No. 508,685, filed Sept. 23, 1974; and P 23 585 92 which corresponds to U.S. application Ser. No. 519,514, filed Sept. 23, 1974.

Azole derivatives which are not per se known can be prepared in accordance with the methods described in the patent applications set forth above.

Tables 1 through 14 below describe representative azole antimycotics which may be used in the compositions of the present invention.

The present invention also includes a method of treating skin conditions caused in whole or in part by *Pityrosporum ovale* which comprises applying to the human skin or other situs of the condition an effective amount of a composition containing an azole antimycotic as above described in combination with a diluent or carrier suitable for application to human skin.

TABLE 1

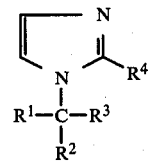

| $R^1$ | $R^2$ | $R^3$ | $R^4$ | Melting point, °C. |
|---|---|---|---|---|
| Phenyl | Phenyl | Phenyl | H | 226–227 |
| p-methylphenyl | Phenyl | Phenyl | H | 128 |

TABLE 1-continued

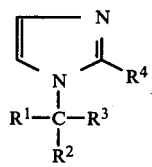

| R¹ | R² | R³ | R⁴ | Melting point, °C. |
|---|---|---|---|---|
| o-Chlorophenyl | Phenyl | Phenyl | H | 140 |
| m-Trifluoromethylphenyl | Phenyl | Phenyl | H | 156 |
| p-Nitrophenyl | Phenyl | Phenyl | H | 160–170 |
| p-Chlorophenyl | m-Fluorophenyl | Phenyl | H | 116 |
| 4-Methylphenyl | 2-Pyridyl | Phenyl | H | 144–145 |
| 2-Ethoxyphenyl | 2-Pyridyl | Phenyl | H | 123–125 |
| 4-Chlorophenyl | 2-Pyridyl | 4-Flurophenyl | H | 138 |
| Phenyl | 4-Pyridyl | Phenyl | $CH_3$ | 175–178 |
| Phenyl | 4-Pyridyl | Phenyl | H | 217–218 |
| Phenyl | 4-Pyridyl | Phenyl | H | 186–200 lactate |
| 4-Chlorophenyl | Phenyl | 1-Imidazolyl | H | 140 |
| 2-Fluorophenyl | 4-Fluorophenyl | 1-Imidazolyl | H | 129 |
| 4-Fluorophenyl | 4-Nitrophenyl | 1-Imidazolyl | H | 198 |
| Phenyl | Phenyl | 1-(2-Methyl)-imidazolyl | $CH_3$ | 193 |
| 4-Bromophenyl | Phenyl | 1-(2-Ethyl)-imidazolyl | $C_2H_5$ | 128 |
| 4-Chlorophenyl | 4-Chlorophenyl | 1-(2-Methyl)-imidazolyl | $CH_3$ | 220 |
| 2,3-Dichlorophenyl | Phenyl | Phenyl | H | 128 |
| 2-Methyl-4-chlorophenyl | Phenyl | Phenyl | H | 158–162 |
| 2-Chlorophenyl | Phenyl | 2-Chlorophenyl | H | 180 |
| 3,4-Dimethylphenyl | Phenyl | 2-Pyridyl | H | 96 |
| 2,6-Dimethylphenyl | Phenyl | 2-Pyridyl | H | 120 hydrochloride |
| 2,3-Dimethylphenyl | Phenyl | 4-Pyridyl | H | 154 |

TABLE 2

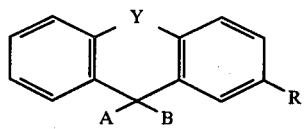

| A | B | R | Y | Melting point, °C. |
|---|---|---|---|---|
| Phenyl | 1-Imidazolyl | H | — | 197–199 |
| 4-Bromophenyl | 1-Imidazolyl | H | — | 181–184 |
| 4-Chlorophenyl | 1-Imidazolyl | H | $-(CH_2)_2-$ | 216–218 |
| Phenyl | 1-Imidazolyl | H | —O— | 160–162 |
| Phenyl | 1-Imidazolyl | H | —S— | 179–181 |
| Phenyl | 1-Imidazolyl | H | —CH=CH— | 208–211 |
| 3-Pyridyl | 1-Imidazolyl | H | — | 80–85 |
| 3-Pyridyl | 1-Imidazolyl | H | $-(CH_2)_2-$ | 147–149 |
| 4-Fluorophenyl | 1-Imidazolyl | H | $-(CH_2)_2-$ | Salicylate, 137–138 |
| 4-Methylthiophenyl | 1-Imidazolyl | H | — | Hydrochloride, from 90 onwards (decomposition) |
| —COOCH₃ | 1-Imidazolyl | H | — | 150 |
| —COOCH₃ | 1-Imidazolyl | Cl | — | 205–210 (decomposition) |
| —COOC₃H₇(n) | 1-Imidazolyl | H | — | 85 |
| —COOCH₃ | 1-(1,2,4-Triazolyl) | H | — | 140–145 |
| —COOC₂H₅ | 1-(1,2,4-Triazolyl) | H | — | 133 |
| —COOCH₃ | 1-(1,2,4-Triazolyl) | Cl | — | 90 (decomposition) |
| —COOC₄H₉ | 1-Imidazolyl | H | — | Hydrochloride, 158 (decomposition) |
| —CH₃ | 1-Imidazolyl | H | — | 139 |
| —CH(CH₃)₂ | 1-Imidazolyl | H | — | 125 |
| —C₂H₅ | 1-Imidazolyl | Cl | — | Hydrochloride, 215 |
| —CH₃ | 1-Imidazolyl | Cl | — | 130 |
| —CH₃ | 1-Imidazolyl | H | —CH=CH— | 188 |
| —CH₂—CH=CH₂ | 1-Imidazolyl | H | $-(CH_2)_2$ | Hydrochloride, 168 |

TABLE 3

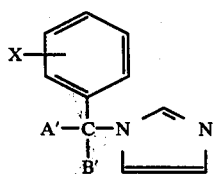

| A' | B' | X | Melting point, °C. |
|---|---|---|---|
| 4-Pyridyl | Cyclohexyl | H | 90 |
| Phenyl | t-Butyl | 4-Cl | 137 |
| 4-Chlorophenyl | t-Butyl | 4-Cl | Hydrochloride, 196 |
| Phenyl | Allyl | H | 80 |
| Phenyl | t-Butyl | 2,5-$(CH_3)_2$ | 112 |
| Phenyl | Cyclopropyl | 3-$CH_3$ | Hydrochloride, 136 |
| 4-Methylphenyl | 1-Methylcyclohexyl | 4-$CH_3$ | 151 |
| Phenyl | t-Butyl | 3-$CH_3$, 4-Cl | 95 |
| Phenyl | 2-Thienyl | 4-F | 144–145 |
| Phenyl | 3-(5-Methyl)-isoxazolyl | 3-$CF_3$ | 69 |
| Phenyl | 2-(1-Methyl)-imidazolyl | H | 200 |
| Phenyl | 5-(3,4-Dichloro)-isothiazolyl | 4-F | 95 |
| Phenyl | (piperazinyl) | H | 209 |
| Phenyl | (trichloropiperazinyl) | H | 142–146 |
| Phenyl | (piperazinyl) | H | 198 |
| 4-Fluorophenyl | (piperazinyl) | H | Hydrochloride |

TABLE 4

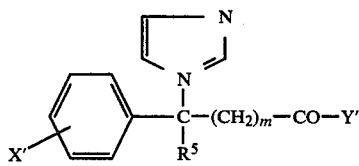

| $R^5$ | X' | Y' | m | Melting point, °C. |
|---|---|---|---|---|
| Phenyl | H | $OCH_3$ | 0 | 155 |
| Phenyl | H | $OCH_3$ | 0 | Sulphate, 145 |
| 2-Methylphenyl | H | $OCH_3$ | 0 | 148 |
| Phenyl | H | $OC_{10}H_{21}$ | 0 | 48 |
| Phenyl | H | $NH(CH_3)_2$ | 0 | 202 |

TABLE 4-continued

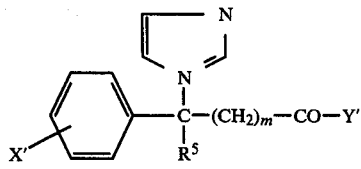

| $R^5$ | X' | Y' | m | Melting point, °C. |
|---|---|---|---|---|
| Phenyl | H | (morpholino) | 0 | Hydrochloride, 118 |
| Phenyl | H | (N-methylpiperazinyl) | 0 | 173 |
| 4-Chlorophenyl | 4-Cl | $OCH_3$ | 0 | 132 |
| 4-Methoxyphenyl | 4-$OCH_3$ | $OCH_3$ | 0 | 131 |
| Phenyl | H | $OC_2H_5$ | 1 | 75 |
| $CH(CH_3)_2$ | H | $OC_2H_5$ | 1 | Hydrochloride, 194 |
| Phenyl | H | $CH_3$ | 0 | 103 |
| 4-Chlorophenyl | H | Phenyl | 0 | 136 |
| 3-Methylphenyl | H | Phenyl | 0 | 120 |

TABLE 5

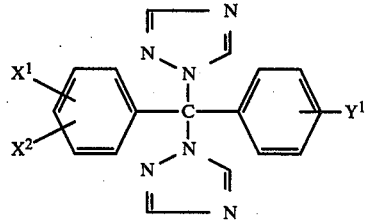

| $X^1$ | $X^2$ | $Y^1$ | Melting point, °C. |
|---|---|---|---|
| H | H | H | 210 |
| H | 2-Cl | H | 205 |
| H | 4-F | 4-CN | 75 |
| 3-$NO_2$ | 4-Cl | H | 84 |
| 5-Cl | 2-Cl | H | 125 |

TABLE 6

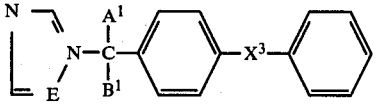

| E | $A^1$ | $B^1$ | $X^3$ | Melting point, °C. |
|---|---|---|---|---|
| CH | Phenyl | Phenyl | — | 173 |
| CH | 2'-(N'—Methylimidazolyl) | Phenyl | — | 134 |
| CH | Phenyl | Phenyl | —S— | 162–164 |
| CH | Phenyl | Phenyl | —CO— | 131–135 |
| CH | Phenyl | Phenyl | —O— | 141–144 |
| CH | 1,5-Dimethylpyrazol-3-yl | Phenyl | —O— | 60 |
| CH | 4-Chlorophenyl | 4-Chlorophenyl | —O— | 136 |
| N | Phenyl | Phenyl | —S— | 137–139 |
| N | 2'-(N'—Methylimidazolyl) | Phenyl | — | 135 |

TABLE 7

Phenylazolyl-fatty-acid derivatives of the general formula:

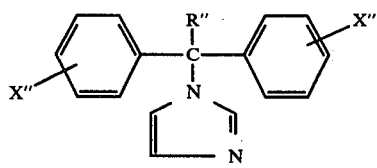

| X″ | Y″ |
|---|---|
| 4-Cl | COO—CH$_2$—CH$_2$—N(CH$_3$)$_2$.2 HCl |
| H | COO—CH(CH$_3$)—CH$_2$—N(CH$_3$)$_2$ |
| H | CONH—CH$_2$—CH$_2$—CH$_2$—N(C$_2$H$_5$)$_2$ |

TABLE 7-continued

Phenylazolyl-fatty-acid derivatives of the general formula:

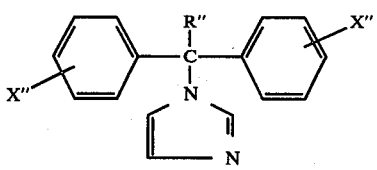

| X″ | Y″ |
|---|---|
| H | COO—CH(CH$_3$)—CH—N(CH$_2$CH$_2$)$_2$O (morpholino) |

Representative compounds include:

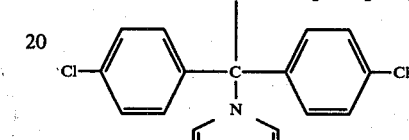

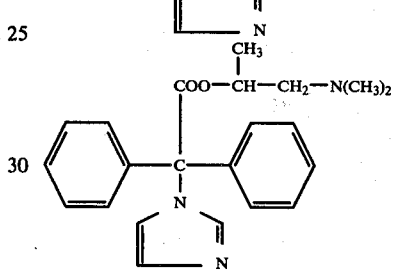

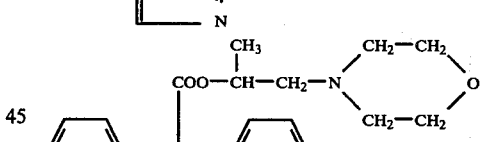

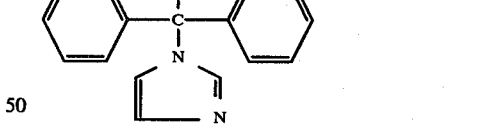

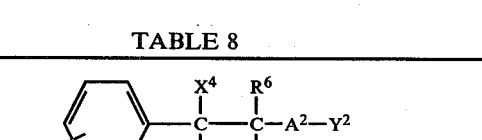

TABLE 8

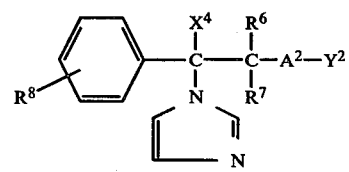

| X$^4$ | Y$^2$ | R$^8$ | R$^6$ | R$^7$ | A$^2$ | Melting point, °C. |
|---|---|---|---|---|---|---|
| Phenyl | H | H | H | H | —O— | 144 |
| Phenyl | CH$_3$—CH$_2$—CO— | H | H | H | —O— | 74 |
| Phenyl | Cl—C$_6$H$_4$—CO— | H | H | H | —O— | 128 |

TABLE 8-continued (structure: phenyl-C(X⁴)(N-imidazole)-C(R⁶)(R⁷)-A²-Y², with R⁸ on phenyl)

| X⁴ | Y² | R⁸ | R⁶ | R⁷ | A² | Melting point, °C. |
|---|---|---|---|---|---|---|
| Phenyl | 3,5-dinitrobenzoyl (NO₂-C₆H₃(NO₂)-CO-) | H | H | H | —O— | 132 |
| Phenyl | C₆H₅-CH=CH-CO- | H | H | H | —O— | 87 |
| Phenyl | CH₃—SO₂— | H | H | H | —O— | 187 |
| Phenyl | CH₃-C₆H₄-SO₂NH-CO- | H | H | H | —O— | 148 |
| Phenyl | CH₃—NHCO—N(CH₃)—CO— | H | H | H | —O— | 140 |
| Phenyl | C₆H₅— | 4-Cl | H | H | —O— | 138 |
| Phenyl | 4-Cl-C₆H₄— | H | CH₃ | CH₃ | —O— | 148 |
| Phenyl | H | H | CH₃ | H | —O— | 154 |
| Phenyl | H | H | C₆H₅ | H | —O— | 203 |
| —C(CH₃)₃ | H | H | H | H | —O— | 130 |
| —C(CH₃)₃ | CH₃—CO— | H | H | H | —O— | 70 |
| Phenyl | 4-Cl-C₆H₄— | H | H | H | —S— | 126 |
| Phenyl | 4-Cl-C₆H₄— | H | H | H | —SO₂— | x CH₃COOH 134 |
| Phenyl | CH₃—CO— | H | H | H | —NH— | 173 |

TABLE 9

(structure: R⁹—C≡C—N(R¹⁰)— attached to phenyl-imidazole system)

| R⁹ | R¹⁰ | Melting point, °C. |
|---|---|---|
| Phenyl | Phenyl | 103–104 |
| Phenyl | 4-Chlorophenyl | 87–87.5 |
| Phenyl | 3-Nitrophenyl | 44–46 |
| Phenyl | C(CH₃)₃ | Oil, $n_D^{25}$ 1.6019 |
| H | Phenyl | 136 |
| CH₃—(CH₂)₄— | Phenyl | Oil, $n_D^{25}$ 1.5755 |
| 2-ethylphenyl (C₂H₅-C₆H₄-) | CH₃ | Oil, $n_D^{25}$ 1.5852 |
| 2-(phenoxymethyl)phenyl (C₆H₅-O-CH₂-C₆H₄-) | | |

TABLE 9-continued $$R^9-C\equiv C-N(R^{10})\text{(imidazolyl)}$$

| $R^9$ | $R^{10}$ | Melting point, °C. |
|---|---|---|
| morpholino-N-CH$_2$- | Phenyl | 63-64 |
| (C$_2$H$_5$)$_2$N-CH$_2$- | Phenyl | 83-84 |

TABLE 10

Thienyl-C(R$^{11}$)(imidazolyl)-A$^3$-X$^5$

| $R^{11}$ | $A^3$ | $X^5$ | Melting point, °C. |
|---|---|---|---|
| Thienyl | —CO— | —OCH$_3$ | 117 |
| Phenyl | —CH$_2$— | —CN | Hydrochloride, 82 |
| 4-Chlorophenyl | —CH$_2$— | —CON(CH$_3$)$_2$ | 161 |
| Thienyl | —CO— | —O—CH(CH$_3$)—CH$_2$—N(CH$_3$)$_2$— | Oil |

TABLE 11

(X$^6$-phenyl)(X$^7$-phenyl)C(imidazolyl)—CO—N(R$^{12}$)(R$^{13}$)

| $X^6$ | $X^7$ | $R^{12}$ | $R^{13}$ | Melting point, °C. |
|---|---|---|---|---|
| H | H | CH$_3$ | 2-methylphenyl | 141-143 |
| 4-Cl | 4-Cl | -(CH$_2$)$_2$SO$_2$(CH$_2$)$_2$- (cyclic) | | 159-163 |
| H | H | 3-CF$_3$-phenyl | H | 219-220 |
| H | H | cyclohexyl | H | 166-168 |
| H | H | 4-(COOC$_2$H$_5$)-piperazinyl | | 156-158 |
| H | H | -CH(phenyl)-CH$_2$-SO$_2$-CH$_2$-CH$_2$- (cyclic) | | 103-104 |

TABLE 12

$$R^{14}-X^8-C(R^{16})(\text{(CH}_2)_n\text{Az})-Y^3-R^{15}$$

| Az | n | $X^8$ | $Y^3$ | $R^{14}$ | $R^{15}$ | $R^{16}$ | Melting point, °C. |
|---|---|---|---|---|---|---|---|
| 1-Imidazolyl | 0 | —O— | —CO— | 2,3-dichlorophenyl | phenyl | H | 218 |
| 1-Imidazolyl | 0 | —O— | —CO— | 4-chlorophenyl | —C(CH$_3$)$_3$ | H | 135 |

TABLE 12-continued $$R^{14}-X^8-\underset{\underset{Az}{(CH_2)_n}}{\overset{R^{16}}{C}}-Y^3-R^{15}$$

| Az | n | $X^8$ | $Y^3$ | $R^{14}$ | $R^{15}$ | $R^{16}$ | Melting point, °C. |
|---|---|---|---|---|---|---|---|
| 1-Imidazolyl | 0 | —O— | —C(OH)$_2$— | 3-Cl-C$_6$H$_4$— | C$_6$H$_5$— | H | Hydrochloride, 124 |
| 1-Imidazolyl | 0 | —O— | —CO— | 4-Cl-C$_6$H$_4$— | C$_6$H$_5$— | CH$_3$ | Oil |
| 1-Imidazolyl | 0 | —S— | —CO— | 4-Cl-C$_6$H$_4$— | —C(CH$_3$)$_3$ | H | Oil |
| 1-Imidazolyl | 0 | —O— | —CO— | 4-Cl-C$_6$H$_4$— | —C(CH$_3$)$_3$ | C$_6$H$_5$— | 98–102 |
| 1-Imidazolyl | 0 | —O— | —C(OH)$_2$— | 2,4-Cl$_2$-C$_6$H$_3$— | C$_6$H$_5$— | H | Hydrochloride 155 |
| 1-Imidazolyl | 0 | —O— | —CO— | 4-Cl-C$_6$H$_4$— | C$_6$H$_5$— | C$_6$H$_5$— | 126 |
| 1-Imidazolyl | 0 | —O— | —CO— | 4-Br-C$_6$H$_4$— | —C(CH$_3$)$_3$ | H | 106 |
| 1-Imidazolyl | 0 | —O— | —CO— | 2,4-Cl$_2$-C$_6$H$_3$— | —C(CH$_3$)$_3$ | C$_6$H$_5$— | Hydrochloride 208 |
| 1-Imidazolyl | 1 | —O— | —CO— | 4-Cl-C$_6$H$_4$— | —C(CH$_3$)$_3$ | H | Hydrochloride 127 |
| 1-Imidazolyl | 1 | —O— | —CO— | 4-F-C$_6$H$_4$— | —C(CH$_3$)$_3$ | H | 102–106 |
| 1-Imidazolyl | 1 | —O— | —CO— | 2,4,5-Cl$_3$-C$_6$H$_2$— | —C(CH$_3$)$_3$ | H | Hydrochloride 180–183 |
| 1-Imidazolyl | 1 | —O— | —CO— | 4-Cl-2-CH$_3$-C$_6$H$_3$— | —C(CH$_3$)$_3$ | H | Hydrochloride 147–150 |
| 1-Imidazolyl | 1 | —O— | —CO— | biphenyl-4-yl— | —C(CH$_3$)$_3$ | H | 111–112 |
| 1-Imidazolyl | 1 | —O— | —CO— | 4-phenyl-3-CH$_2$OH-C$_6$H$_3$— | —C(CH$_3$)$_3$ | H | 105–107 |
| 1-Imidazolyl | 1 | —O— | —CO— | 4-CH$_3$-C$_6$H$_4$— | —C(CH$_3$)$_3$ | H | Hydrochloride 135 |

TABLE 12-continued $$R^{14}-X^8-\underset{\underset{Az}{(CH_2)_n}}{\overset{R^{16}}{C}}-Y^3-R^{15}$$

| Az | n | $X^8$ | $Y^3$ | $R^{14}$ | $R^{15}$ | $R^{16}$ | Melting point, °C. |
|---|---|---|---|---|---|---|---|
| 1-Imidazolyl | 1 | —O— | —CO— | 2,3-dimethylphenyl | —C(CH$_3$)$_3$ | H | Hydrochloride 143–147 |
| 1-Imidazolyl | 1 | —O— | —CO— | 3-chloro-4-nitrophenyl | —C(CH$_3$)$_3$ | H | 122–123 |
| 1-Imidazolyl | 1 | —O— | —CO— | 4-chlorophenyl | cyclohexyl | H | Hydrochloride 148–150 |
| 1-(1,2,4-Triazolyl) | 0 | —O— | —CO— | 2,4-dichlorophenyl | 4-chlorophenyl | H | 101–104 |
| 1-(1,2,4-Triazolyl) | 0 | —O— | —CO— | 4-chloro-3-methylphenyl | —C(CH$_3$)$_3$ | H | 94–96 |
| 1-(1,2,4-Triazolyl) | 0 | —O— | —CO— | 4-nitrophenyl | —C(CH$_3$)$_3$ | H | 145 |
| 1-(1,2,4-Triazolyl) | 0 | —O— | —CO— | 4-biphenylyl | —C(CH$_3$)$_3$ | H | 105–106 |
| 1-(1,2,4-Triazolyl) | 0 | —O— | C=NOH | 4-nitrophenyl | —C(CH$_3$)$_3$ | H | 187 |
| 1-(1,2,4-Triazolyl) | 0 | —O— | C(OH)$_2$ | pentachlorophenyl | —C(CH$_3$)$_3$ | H | 206–207 |
| 1-(1,2,4-Triazolyl) | 0 | —O— | —CO— | 4-chlorophenyl | —C(CH$_3$)$_3$ | H | Sulfate 141 |
| 1-(1,2,4-Triazolyl) | 0 | — | —CO— | phenyl | —C(CH$_3$)$_3$ | phenyl | 99 |
| 1-(1,2,4-Triazolyl) | 0 | —O— | —CHOH— | 4-tert-butylphenyl | —C(CH$_3$)$_3$ | H | 113–117 |
| 1-(1,2,4-Triazolyl) | 0 | —O— | —CHOH— | 4-fluorophenyl | —C(CH$_3$)$_3$ | H | 99–110 |
| 1-(1,2,4-Triazolyl) | 0 | —O— | —CHOH— | 2,3-dimethylphenyl | —C(CH$_3$)$_3$ | H | 133–135 |

TABLE 12-continued $$R^{14}-X^8-\underset{\underset{Az}{\overset{\displaystyle (CH_2)_n}{|}}}{\overset{\displaystyle R^{16}}{\underset{|}{C}}}-Y^3-R^{15}$$

| Az | n | X⁸ | Y³ | R¹⁴ | R¹⁵ | R¹⁶ | Melting point, °C. |
|---|---|---|---|---|---|---|---|
| 1-(1,2,4-Triazolyl) | 0 | —O— | —CCH₃OH— | 2,5-dichlorophenyl  | —C(CH₃)₃ | H | 101–103 |
| 1-(1,2,4-Triazolyl) | 0 | —O— | —CCH₃OH— | 4-chlorophenyl  | phenyl  | H | 171–173 |
| 1-(1,2,4-Triazolyl) | 0 | —O— | —CHOH | 3,4-dichlorobiphenyl  | —C(CH₃)₃ | H | 142–144 |
| 1-Imidazolyl | 0 | —O— | —CHOH | 4-chlorophenyl  | —C(CH₃)₃ | H | 145–147 |
| 1-Imidazolyl | 0 | —O— | —CHOH— | 4-bromophenyl  | —C(CH₃)₃ | H | 173–174 |
| 1-Imidazolyl | 0 | —O— | —CHOH | 4-tert-butylphenyl 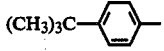 | —C(CH₃)₃ | H | 145–150 |
| 1-Imidazolyl | 0 | —O— | —CHOH— | biphenyl 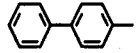 | —C(CH₃)₃ | H | 136–148 |
| 1-Imidazolyl | 0 | —O— | —CHOH— | 2,4-dichlorophenyl  | —C(CH₃)₃ | H | Hydrochloride 190–210 |
| 1-Imidazolyl | 0 | —O— | —CHOH— | 2,4-dichlorophenyl  | —C(CH₃)₃ | phenyl  | 159–160 |
| 1-(1,2,4-Triazolyl) | 1 | —O— | —CO— | 4-methylphenyl 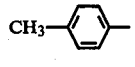 | —C(CH₃)₃ | H | 42–44 |
| 1-(1,2,4-Triazolyl) | 1 | —O— | —CO— | 4-chloro-2-methylphenyl 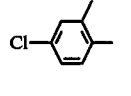 | —C(CH₃)₃ | H | 63–65 |
| 1-(1,2,4-Triazolyl) | 1 | —O— | —CO— | 3-chlorophenyl  | —C(CH₃)₃ | H | 73–74 |
| 1-(1,2,4-Triazolyl) | 1 | —O— | —CO— | 4-nitrophenyl 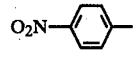 | —C(CH₃)₃ | H | 97–98 |
| 1-(1,2,4-Triazolyl) | 1 | —O— | —CHOH— | 2-chlorophenyl  | —C(CH₃)₃ | H | 106–108 |
| 1-(1,2,4-Triazolyl) | 1 | —O— | —CHOH— | 2,6-dimethylphenyl 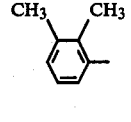 | —C(CH₃)₃ | H | 132–134 |

TABLE 12-continued $$R^{14}-X^8-\underset{\underset{Az}{\underset{|}{(CH_2)_n}}}{\overset{\overset{R^{16}}{|}}{C}}-Y^3-R^{15}$$

| Az | n | $X^8$ | $Y^3$ | $R^{14}$ | $R^{15}$ | $R^{16}$ | Melting point, °C. |
|---|---|---|---|---|---|---|---|
| 1-(1,2,4-Triazolyl) | 1 | —O— | —CHOH— | F—⌬— | —C(CH$_3$)$_3$ | H | 121–122 |
| 1-(1,2,4-Triazolyl) | 1 | —O— | —CCH$_3$OH— | Cl—⌬— | —C(CH$_3$)$_3$ | H | 150 |
| 1-Imidazolyl | 1 | —O— | —CHOH— | ⌬—(o-Cl) | —C(CH$_3$)$_3$ | H | 162–163 |
| 1-Imidazolyl | 1 | —O— | —CHOH— | Cl—⌬—CH$_3$ | —C(CH$_3$)$_3$ | H | 163–164 |
| 1-Imidazolyl | 1 | —O— | —CCH$_3$OH— | Cl—⌬— | —C(CH$_3$)$_3$ | H | 155 |
| 1-Imidazolyl | 1 | —O— | —C(CH$_2$—C$_6$H$_5$)OH— | Cl—⌬— | —C(CH$_3$)$_3$ | H | 179–181 |

TABLE 13

| $R^{17}$ | Melting point, °C. |
|---|---|
| H | 110–112 |
| —C(CH$_3$)$_3$ | 114–118 |
| 2-Cl-C$_6$H$_4$— | 152–154 |
| C$_6$H$_{11}$— (cyclohexyl) | 170–171 |
| —CH(CH$_3$)—C$_2$H$_5$ | 156–158 |

*Pityrosporum ovale* is a blastomycete which is only parasitic in the uppermost layers of human skin, particularly in excessively greasy skin. It is regarded as the cause of the following changes in skin, which are not regarded as skin diseases:

(1) *Pityriasis simplex,* (2) *Pityriasis oleosa* and (3) *Pityriasis circinata.* It is also regarded as the cause of the following, which are considered to be skin diseases: seborrhoeic dermatitis and *Acne vulgaris* (as coexistent germ).

All the skin conditions caused, or partially caused, by *Pityrosporum ovale* are grouped under the generic term "seborrhoea".

Other coexistent germs found in seborrhoea are: *Staph. albus* and *corynebacteria,* as well as *Malassezia furfur.* The latter are also known as the pathogens of erythrasma and of Pityriasis versicolor.

Seborrhoea is widespread and is frequently one of the causes of loss of hair and formation of scaly skin, especially on the scalp.

Seborrhoeic eczemas also occur very frequently on the face and are therefore objectionable and disturbing. They are *not a medicinal* problem but a *cosmetic* problem.

The activities of the compounds used in this invention were tested as follows:

*Pityrosporum ovale* was cultured and the MIC determinations were carried out with a large number of azole derivatives. The growth of *Pityrosporum ovale* is considerably slower than, for example, of species of Candida or Torulopsis—it takes 3 to 5 days. It requires Abbe's medium as a special nutrient medium.

Procedure:

1. Setting up the dilution series of each preparation: 6.4 mg of preparation are dissolved in 1 ml of analytical grade dimethylformamide and 9 ml of distilled water are added. 1 ml now contains 640 mcg of preparation. If 2 ml are withdrawn and added to 2 ml of H$_2$O, the resulting concentration is 320 mcg/ml. If this is continued progressively, the following dilution series, in mcg/ml, is obtained: 640-320-160-80-40-20-10-5-2.-5-1.25-0.625-0.313-0.156-0.078-0.039-0.02-0.01.

2. Charging the test tubes: 0.5 ml portions of the particular dilution are introduced into test tubes.

3. Charging with nutrient medium: Abbe's medium is used.
Recipe:
15.0 g of malt extract (Messrs. Diamalt)
+2.5 g of peptone (Messrs. BBL)
+10.0 g of ox bile (Messrs. Merck)
+20.0 g of agar-agar (Messrs. Difco)
+100.0 g of Tween 40 mixture
+900.0 g of distilled water.

Tween 40 mixture: 100 ml of Tween 40 (Merck)+400 ml of distilled water+25 g of highest purity glycerol (Merck) are mixed and then made up to 1,000 ml with distilled water.

200 ml portions of Abbe's medium are introduced into nutrient medium flasks. For use, the previously calculated amount of Abbe's medium is liquefied in a steaming pot and cooled until only warm to the touch; 4.5 ml are then added to each test tube. A second person receives each test tube and twirls it between his hands, like a kitchen whisk. This achieves good mixing of the diluted preparation with the nutrient medium. Each test tube is then immediately brought into a slanting position, in the same way as is usually employed to prepare agar slants.

The final concentrations of the various preparations are then, in mcg/ml of test medium: 64-32-16-8-4-2-1-0.5-0.25-0.125-0.062-0.031-0.016-0.0-08-0.004-0.002-0.001.

The culture control and the nutrient medium control are each 1 test tube in which 0.5 ml of $H_2O$ is introduced in place of the preparation.

4. Inoculation with *Pityrosporum ovale:* A culture which had been grown for 3 weeks in Benham's fluid medium at 28° C. was used.
Recipe for Benham's fluid medium:
1.0 g of $KH_2PO_4$
0.5 g of $MgSO_4.7H_2O$
1.25 g of asparagine
500 ml of distilled water
500 ml of 4% strength Tween 80 in $H_2O$
bring to pH 6.4 with NaOH.

After the nutrient medium has solidified thoroughly in all the test tubes, 0.1 ml of culture is allowed to run over each slant, except for the test tube of the nutrient medium control. 0.1 ml of physiological NaCl solution is added to the latter.

5. Incubation and readings: The incubation is carried out at 28° C. After 3 days, the culture control test tubes show germ growth, which reaches an optimum after 5 days.

The MIC=minimum inhibitory concentration, and the PI=partial inhibition (retardation of growth by about 90% relative to the control, that is to say only about 10% of the germs have grown) are read off in comparison to the control.

Of course,—as is usual in microbiology—all the work was carried out under sterile conditions, that is to say, using, for example, sterile test tubes, pipettes, nutrient media and the like.

Table 14 which follows lists the MIC values=minimum inhibitory concentrations, and PI values=partial inhibitions of a representative selection of the azole antimycotics claimed.

As shown by these results the azole antimycotics of the present invention can be used as additives to cosmetics and hair lotions, particularly since the azole group is also active against *Staph. albus* and *corynebacteria* at levels of 2 γ/ml.

TABLE 14

| MIC and PI values of *Pityrosporum ovale* in the presence of various azole derivatives | | | | |
|---|---|---|---|---|
| | Reading after 3 days | | Reading after 5 days | |
| Compound (Example No.) | MIC mcg/ml | PI* mcg/ml | MIC mcg/ml | PI* mcg/ml |
| (1) 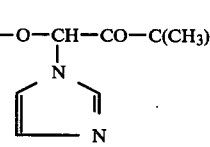 | <1 | | <1 | |
| (2) 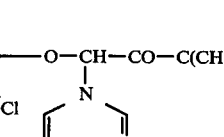 | <1 | | <1 | |
| (3) 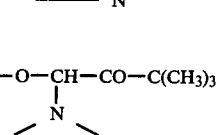 | <1 | | <1 | |

TABLE 14-continued

MIC and PI values of *Pityrosporum ovale* in the presence of various azole derivatives

| Compound (Example No.) | Reading after 3 days MIC mcg/ml | Reading after 3 days PI* mcg/ml | Reading after 5 days MIC mcg/ml | Reading after 5 days PI* mcg/ml |
|---|---|---|---|---|
| (4) Cl–⌬–⌬–O–CH(–CO–C(CH$_3$)$_3$)–N(imidazole) × HCl | <1 | | <1 | |
| (5) 2,4-Cl$_2$C$_6$H$_3$–O–CH(–CO–C(CH$_3$)$_3$)–CH$_2$–N(imidazole) × HCl | 2 | <1 | 2 | <1 |
| (6) Cl–C$_6$H$_4$–O–CH(–CO–C(CH$_3$)$_3$)–CH$_2$–N(imidazole) | 2 | <1 | 2 | <1 |
| (7) biphenyl–O–CH(–CH(OH)–C(CH$_3$)$_3$)–N(imidazole) | 4 | 2 | 8 | 2 |
| (8) Cl–C$_6$H$_4$–O–CH(–CO–C(CH$_3$)$_3$)–CH$_2$–N(imidazole) × HCl | 4 | 2 | 8 | 4 |
| (9) fluorenyl–N(imidazole), o-CH$_3$ | 8 | 2 | 8 | 4 |
| (10) HC≡C–C(Ph)$_2$–N(imidazole) | 8 | <1 | 16 | <1 |
| (11) (Ph)$_2$C(COOCH$_3$)–N(imidazole) | 16 | <1 | 16 | <1 |

TABLE 14-continued

MIC and PI values of *Pityrosporum ovale* in the presence of various azole derivatives

| Compound (Example No.) | Reading after 3 days | | Reading after 5 days | |
|---|---|---|---|---|
| | MIC mcg/ml | PI* mcg/ml | MIC mcg/ml | PI* mcg/ml |
| (12) [biphenyl-O-CH(CH₂-imidazolyl)-CO-C(CH₃)₃] | 8 | <1 | 8 | <1 |
| (13) [(2-chlorophenyl)(diphenyl)C-imidazolyl] | 16 | 8 | 16 | 8 |
| (14) [ethyl(diphenyl)C-imidazolyl] | 32 | 4 | 32 | 4 |
| (15) [CO-CH₃, diphenyl C-imidazolyl] | 32 | 4 | 64 | 4 |
| (16) [(4-chlorophenyl)(diphenyl)C-imidazolyl] | >64 | 16 | >64 | 16 |
| (17) [(3-chlorophenyl)(phenyl)C(imidazolyl)₂] | >64 | 32 | >64 | 32 |
| (18) [dibenzocycloheptane-CH₃-imidazolyl] | >64 | 32 | >64 | 32 |
| (19) [(2,4-dichlorophenyl)-O-C(phenyl)(imidazolyl-CH₂)-CH(OH)-C(CH₃)₃] | >64 | 64 | >64 | 64 |

TABLE 14-continued

MIC and PI values of *Pityrosporum ovale* in the presence of various azole derivatives

| Compound (Example No.) | Reading after 3 days | | Reading after 5 days | |
|---|---|---|---|---|
| | MIC mcg/ml | PI* mcg/ml | MIC mcg/ml | PI* mcg/ml |
| (20) | >64 | 64 | >64 | 64 |
| (21) | >64 | | >64 | |
| (22) | >64 | | >64 | |

+Partial inhibition was recorded if the growth of the cultures was reduced by at least 90% compared to the control.

According to the present invention, the azole antimycotics can be used in many diverse cosmetic preparations. The following hair toiletries and hairdressing preparations may be mentioned as examples: hair soaps, hair creams, hair lotions, hair tonics, hair oils, hair pomades, hair brilliantines and especially hair rinses and shampoos. The following may be mentioned as examples of skin toiletries: soap and detergent compositions in the form of bars, liquids or powders, fluid creams and skin gels, skin oils, face lotions, astringents and deodorants.

Where the azole antimycotic is incorporated into a shampoo, the shampoo may be a clear liquid, an opaque liquid, a gel, a cream or a powder.

In any interaction of the shampoo with the hair and skin or scalp a decisive factor is whether the surface-active compounds (detergents) on which the shampoos are based are anionic or cationic or non-ionic surfactants or whether they are combinations of these substances. The surface-active compound will normally be present in shampoo compositions of the invention in an amount of at least 30% by weight, preferably at least 70% by weight.

The following may be mentioned as examples of such anionic surface-active substances: $C_{10}$–$C_{20}$-alkyl-carboxylates and alkylene-carboxylates, alkyl-ether-carboxylates, fatty alcohol sulphates, fatty alcohol-ether sulphates, alkylolamide-sulphates and alkylolamide-sulphonates, fatty acid alkylol-amide-polyglycol ether sulphates, alkanesulphonates and hydroxyalkanesulphonates, olefinesulphonates, acyl esters of isethionates, $\alpha$-sulpho-fatty acid esters, alkylbenzenesulphonates, alkylphenol glycol ether-sulphonates, sulphosuccinates, sulphosuccinic acid half-esters and diesters, fatty alcohol-ether phosphates, albumen-fatty acid condensation products, alkyl monoglyceride sulphates and sulphonates, alkyl glyceride-ether sulphonates, fatty acid methyltaurides, fatty acid sarcosinates and sulphoricinoleates. These compounds and their mixtures may be used in the form of their water-soluble or water-dispersible salts, for example the sodium, potassium, magnesium, ammonium, monoethanolammonium, diethanolammonium and triethanolammonium and analogous alkylolammonium salts.

Suitable cationic surfactants are, for example, quaternary ammonium salts such as di-($C_{10}$–$C_{24}$-alkyl)-dimethylammonium chloride or bromide, preferably di-($C_{12}$–$C_{18}$-alkyl)-dimethylammonium chloride or bromide; $C_{10}$–$C_{24}$-alkyl-dimethylethylammonium chloride or bromide; $C_{10}$–$C_{24}$-alkyl-trimethylammonium chloride or bromide, preferably cetyl-trimethylammonium chloride or bromide and $C_{20}$–$C_{22}$-alkyl-trimethylammonium chloride or bromide; $C_{10}$–$C_{24}$-alkyl-dimethylbenzylammonium chloride or bromide, preferably $C_{12}$–$C_{18}$-alkyldimethyl-benzylammonium chloride; N-($C_{10}$–$C_{18}$-alkyl)-pyridinium chloride or bromide, preferably N-($C_{12}$–$C_{16}$-alkyl)-pyridinium chloride or bromide; N-($C_{10}$–$C_{18}$-alkyl)-isoquinolinium chloride, bromide or monoalkyl-sulphate; N-($C_{12}$–$C_{18}$-alkylolcolaminoformylmethyl)-pyridinium chloride; N-

($C_{12}$–$C_{18}$-alkyl)-N-methyl-morpholinium chloride, bromide or monoalkylsulphate; N-($C_{12}$–$C_{18}$-alkykl)-N-ethyl-morpholinium chloride, bromide or monoalkyl-sulphate; $C_{16}$–$C_{18}$-alkyl-pentaoxethylammonium chloride; diisobutyl-phenoxyethoxyethyldimethylbenzylammonium chloride; salts of N,N-diethylaminoethyl-stearylamide and -oleylamide with hydrochloric acid, acetic acid, lactic acid, citric acid and phosphoric acid; N-acylamidoethyl-N,N-diethyl-N-methylammonium chloride, bromide or monoalkyl-sulphate and N-acylamidoethyl-N,N-diethyl-N-benzylammonium chloride, bromide or monoalkyl-sulphate, wherein acyl is preferably stearyl or oleyl.

Non-ionic detergents can only be used with adjuvants since they have a low foaming power. They include lyophilic higher-molecular esters of aliphatic polyhydric alcohols with aliphatic polycarboxylic acids, and polyglycol esters of fatty acids. The following may be mentioned as individual examples: fatty alcohol ethoxylates (alkylpolyethylene glycols); alkylphenol-polyethylene glycols; alkylmercaptan-polyethylene glycols; fatty amine ethoxylates (alkylamine-polyethylene glycols); fatty acid ethoxylates (acid-polyethylene glycols); polypropylene glycol ethoxylates (Pluronic ®); fatty acid alkylolamides (fatty acid amidepolyethylene glycols); sucrose esters; sorbitol esters and polyglycol ethers.

Examples of amphoteric surfactants which can be added to the shampoos are: N-($C_{12}$–$C_{18}$-alkyl)-β-aminopropionates and N-($C_{12}$–$C_{18}$-alkyl)-β-iminodipropionates as alkali metal salts and mono-, di- and tri-alkylolammonium salts; N-acylamidoalkyl-N,N-dimethyl-acetobetaine, preferably N-($C_8$–$C_{18}$-acyl)-amidopropyl-N,N-dimethyl-acetobetaine; $C_{12}$–$C_{18}$-alkyldimethyl-sulphopropyl-betaine; amphoteric surfactants based on imidazoline (for example: Miranol ® or Steinapon ®), preferably the sodium salt of 1-(β-carboxy-methyloxyethyl)-1-(carboxymethyl)-2-lauryl-imidazolinium; amine oxides, for example $C_{12}$–$C_{18}$-alkyldimethylamine oxide and fatty acid amido-alkyl-dimethylamine oxide.

The compositions of the present invention can, furthermore, contain other additives customary in cosmetics, for example perfumes, dyestuffs, including those which at the same time dye or tint the hair, solvents, opacifying agents or pearlescent agents, for example esters of fatty acids with polyols, magnesium salts and zinc salts of fatty acids, dispersions based on copolymers, thickeners such as sodium chloride, potassium chloride, ammonium chloride and sodium sulphate, fatty acid alkylolamides, cellulose derivatives, natural gums, plant extracts, albumen derivatives such as gelatine, collagen hydrolysis products, natural or synthetic polypeptides, egg yolk, lecithin, lanolin and lanolin derivatives, fats, oils, fatty alcohols, silicones, deodorants, anti-microbial substances, anti-seborrhoeic substances, materials having a keratolytic and keratoplastic action such as, for example, sulphur, salicylic acid and enzymes.

The above-mentioned cationic surfactants can also be present in other preparations, such as, for example, in hair rinses, hair tonics and hair regenerating agents and in anhydrous oily preparations, such as hair oil, hair pomade and hair brilliantine. The preparations of the antimycotically active azole derivatives can also be offered in the form of aqueous and aqueous-alcoholic hair lotions, wave-setting lotions (hair fixatives), including such preparations in the form of gels, and in the form of aerosols as hair sprays as well as in the form of hair toiletry creams and gels and hairdressing creams and gels.

Ethanol and isopropanol are the preferred alcohols for use in these preparations.

These and all preparations already mentioned previously are produced in a conventional manner by bringing together the individual components, of the mixture, including the azole antimycotic, and processing the mixture appropriately to the type of preparation concerned.

The various cosmetic preparations containing the azole antimycotic can be used in the customary manner, preferably by rubbing or massaging into the scalp.

The azole antimycotics used in the present invention, especially the compounds (1) to (8) in Table 14, can preferably be present in the various preparations in concentrations of 0.05% to 5%, preferably 0.1% to 1%, by weight. Within this range, the concentrations of the special preparations depend on their intended use. Certain preparations, such as, for example, concentrates which have to be diluted before use, may also contain higher concentrations.

The following preparations exemplify various compositions according to the present invention:

| Example A: Shampoo (liquid) | |
|---|---|
| Sodium lauryl-ether-sulfate | 50.0% |
| Coconut fatty acid diethanolamide | 5.0% |
| Water | 44.0% |
| Azole antimycotic | 1.0% |
| Preservative, dyestuff, perfume | q.s. |
| Example B: Shampoo (liquid) | |
| Monoethanol ammonium lauryl sulfate | 50.0% |
| Oleic acid diethanolamide | 3.5% |
| Water | 45.5% |
| Azole antimycotic | 1.0% |
| Preservative, dyestuff, perfume | q.s. |
| Example C: Shampoo (cream) | |
| Sodium salt of the condensation product of saturated fatty acids of medium chain length and methyltaurine (approx. 30% content of active substance) | 70.0% |
| Sodium salt of the condensation product of higher-molecular saturated fatty acids and methyllaurine (approx. 30% content of active substance) | 15.0% |
| Fatty acid polyglycol ester (as an opacifying agent) | 3.0% |
| Sodium salt of the condensation product of saturated fatty acids of average chain length and sarcosine (approx. 65% content of active substance) | 3.0% |
| Water | 8.0% |
| Azole antimycotic | 1.0% |
| Preservative, dyestuff, perfume | q.s. |
| Example D: Shampoo (in aerosol form) | |
| Sodium lauryl-ether-sulphate (27%–28% content of active substance) | 55.0% |
| Sodium lauryl-sulphate (>90% of content of active substance) | 5.0% |
| Coconut fatty acid diethanolamide | 3.0% |
| Azole antimycotic | 1.0% |
| Water | 36.0% |
| Preservative, dyestuff, perfume | q.s. |
| Packaged as: 92% of the shampoo of the above | |

-continued

| | |
|---|---|
| composition and 8% of a propellant mixture of dichlorodifluoromethane/1,1,2,2-tetrafluorodichloroethane (40:60) | |
| Example E: Shampoo (powder) | |
| Sodium oleyl-methyltauride (approx. 64% content of active substance) | 32.0% |
| Sodium tripolyphosphate of sodium hexametaphosphate | 3.0% |
| Dried sodium sulphate | 64.0% |
| Azole antimycotic | 1.0% |
| Anti-caking agent, for example, calcium stearate of highly dispersed amorphous silica or products based on CaO/P$_2$O$_5$/SiO$_2$, perfume oil and dyestuff | q.s. |
| Example F: Hair lotion | |
| Isopropanol | 50.0% |
| Vitamin H | 0.2% |
| Diisopropyladipate | 1.0% |
| Perfume oil H + R | 1.0% |
| Water | 47.0% |
| Inositol | 0.3% |
| Azole antimycotic | 0.5% |
| Example G: Hair fixative | |
| Copolymer of 50 parts of vinyl acetate and 50 parts of N—vinylpyrrolidone (approx. 50% content of active substance in isopropanol solution) | 6.0% |
| Isopropanol | 45.0% |
| Azole antimycotic | 0.5% |
| Pentaoxethyl-stearyl-ammonium chloride (approx. 20% content of active substance) | 2.0% |
| Perfume oil | q.s. |
| Water | ad 100.0% |
| Example H: Skin Oil | |
| Oleic acid decyl ester | 30.0% |
| Capryl/capric acid-triglyceride | 30.0% |
| 1-(4-chlorphenoxy)-1-(1-imidazolyl)-3,3-dimethyl-2-butanone(I) | 1.0% |
| Low viscosity paraffin | 39.0% |
| Mix and warm to 90° C. until compound I is dissolved. Then cool. | |
| Example I: Face Lotion | |
| A: Cetylstearyl alcohol with 12 moles ethylene oxide | 3.0% |
| Mixture of mono- and di-glycerides of palmitic and stearic acids | 9.0% |
| Capryl/capric acid-triglyceride | 5.0% |
| Low viscosity paraffin | 3.0% |
| 1-(4-Chlorphenoxy)-1-(1-imidazolyl-3,3-dimethyl-2-butanone(I) | 1.0% |
| B: Anhydrous glycerine | 8.0% |
| Demineralized water | ad 100.0% |
| Preservative and perfume | q.s. |
| A: Heat to 85° C. until compound I has dissolved. Then cool to 70° C. | |
| B: Heat to 70° C. to emulsify and homogenize A in B. | |
| Example J: Cream | |
| A: Cetylstearyl alcohol with 12 moles ethylene oxide | 3.0% |
| Mixture of mono- and di-glyceride of palmitic and stearic acids | 14.0% |
| 2-Octyldecanol | 20.0% |
| Capryl/Capric Acid-Triglyceride | 8.0% |
| 1-(4-Chlorphenoxy)-1-(1-imidazolyl)-3,3-dimethyl-2-butanone(I) | 1.0% |
| B: 1,2-Propyleneglycol | 5.0% |
| Demineralized water | ad 100.0% |
| A: Heat to 80° C. until compound I is dissolved. Then cool to 70° C. | |
| B: Heat to 75° C. and emulsify A in B. | |
| Example K: Cream | |
| A: Glycerine-Sorbitan-Fatty acid ester | 8.00% |
| Low viscosity paraffin oil | 8.00% |
| Capryl/Capric Acid-Triglyceride | 20.00% |
| 1-(4-Chlorphenoxy)-1-(1-imidazolyl-3,3-dimethyl-2-butanone(I) | 1.00% |
| B: Demineralized water | ad 100.00% |
| Preservative and perfume | q.s. |
| A: Heat to about 80° C. until compound I is dissolved. Then cool to 70° C. | |
| B: Heat to 75° C. and emulsify A in B. | |

The following nonlimitative examples more particularly illustrate the present invention:

EXAMPLES OF THE PREPARATION OF THE CHEMICALS

Example (1)

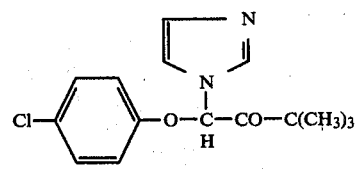

Charge: 15.25 g (0.05 mol) of [1-bromo]-[1-(4'-chloro)phenoxy]-3-dimethyl-butan-2-one and 12 g (0.18 mol) of imidazole.

The two components were dissolved in 120 ml of acetonitrile and the solution was then heated to the boil under reflux for 18 hours. After distilling off the solvent in vacuo, 150 ml of water and 120 ml of methylene chloride were added to the residue and the organic phase was then separated off and additionally treated three times with 30 ml of water at a time, and dried, and the solvent was distilled off in vacuo. After recrystallizing the residue from about 400 ml of ligroin, 10.5 g (72% of theory) of [1-imidazolyl-(1)]-[1-(4'-chloro)-phenoxy]-3-dimethyl-butane-2-one of melting point 135° C. were obtained.

1-Bromo-1-[(4'-chloro)-phenoxy]-3-dimethyl-butane-2-one, used as the starting material, was obtained from 4-chlorophenol and bromopinacolone, followed by bromination with bromine at 140° C. (melting point 80° C.).

The following compounds were produced in an analogous manner to that set forth in Example 1 above:

Example (2)

The compound

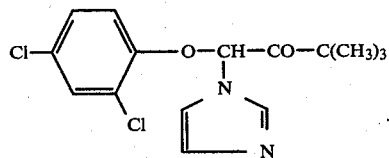

was produced in a manner analogous to that set forth in Example 1.

Example (3)

The compound

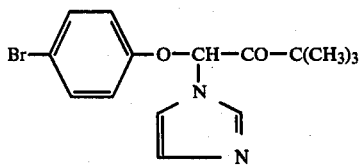

was produced in a manner analogous to that set forth in Example 1.

Example (4)

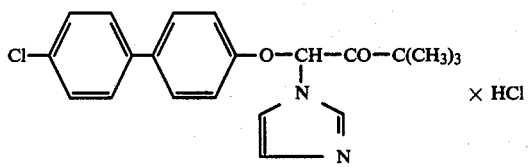

605 g (2 mols) of [1-(4'-(4''-chlorophenyl)-phenoxy]-3,3-dimethyl-butan-2-one were dissolved in 3 l of methylene chloride. 170 ml (2.1 mols) of sulphuryl chloride were added dropwise at 40° C. over the course of 2 to 3 hours and the mixture was then stirred for 15 hours at this temperature. Thereafter the solvent was distilled off in vacuo and the residue was dissolved in 1.5 l of methyl ethyl ketone. This solution was added dropwise, with slight cooling, at 20° C., to a suspension of 280 g (4 mols) of imidazole and 280 g (2 mols) of powdered potassium carbonate in 3 l of methyl ethyl ketone. After stirring for 48 hours at room temperature, the solvent was distilled off. The residue was taken up in 3 l of methylene chloride, washed with four times 1 l of water and then dried over sodium sulphate, and the solvent was distilled off in vacuo. The oil which remains was recrystallized from 1 liter of diisopropyl ether.

This crude base was dissolved in approx. 1.2 l of methylene chloride. 550 ml of approx. 4N hydrochloric acid in ether were added cautiously and the solvent distilled off. 1 liter of ethyl acetate was then added to the oil which remained and the mixture was heated, whereupon spontaneous crystallization occurred. After heating for ½ hour, the crystals were filtered off hot, washed with a little ethyl acetate and dried in vacuo. After two recrystallisations from acetone, 210 g (26% of theory) of [1-imidazolyl-(1)]-[1-(4'-(4''-chlorophenyl)-phenoxy]-3,3-dimethyl-butan-2-one hydrochloride of melting point 148°-150° C. are obtained.

Starting Product

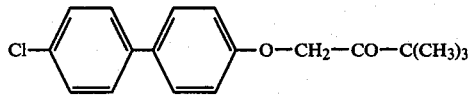

280 g (2 mols) of powdered potassium carbonate were suspended in 2 l. of methyl ethyl ketone. 409 g (2 mols) of 4'-chloro-hydroxybiphenyl were added and the mixture was heated to the boil. Thereafter 260 g (2 mols) of α-chloropinacolone were added dropwise over the course of 1 hour and the mixture was heated under reflux for 15 hours. After cooling, the solid residue was filtered off, washed and recrystallised from ligroin. 513 g (79% of theory) of [1-(4'-(4''-chlorophenyl)-phenoxy]-3,3-dimethyl-butan-2-one of melting point 90° C. are obtained.

Example (5)

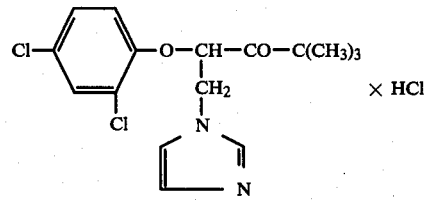

29.1 g (0.1 mol) of 2-(2,4-dichlorophenoxy)-1-hydroxy-4,4-dimethyl-pentan-3-one were taken up in 200 ml of toluene, 10.2 g (0.14 mol) of imidazole were added dropwise thereto and the reaction solution was boiled for 3 hours under a water separator. Thereafter the solvent was distilled off in vacuo, 100 ml of water were added to the oil obtained and the mixture was extracted with twice 100 ml of methylene chloride.

The organic phase was washed with twice 50 ml of water and dried over sodium sulphate, and the solvent was distilled off in vacuo.

An oil was obtained which was taken up in 50 ml of ether, and 50 ml of ether saturated with dry hydrogen chloride were added. The solvent was distilled off in vacuo, the resulting oil was taken up in a mixture of 500 ml of ligroin and 300 ml of ethyl acetate and the mixture was heated to the boil under reflux. After carefully decanting the resulting solution, and cooling it, 18.5 g (49% of theory) of 2-(2,5-dichlorophenoxy)-4,4-dimethyl-1-(1-imidazolyl)-pentan-3-one hydrochloride precipitated as colourless crystals which were isolated by filtration.

Melting point: 118° C.

Starting Material

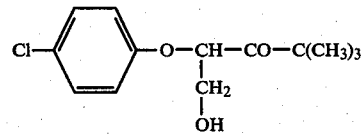

26.1 g (0.1 mol) of 1-(2,4-dichlorophenoxy)-3,3-dimethyl-butan-2-one were dissolved in 200 ml of ethanol and 20 g (0.24 mol) of 40% strength formaldehyde solution were added, followed by about 5 ml of 10% strength sodium hydroxide solution until the pH was 9. The reaction mixture was heated under reflux for 3 hours and the solvent was distilled off in vacuo. The resulting precipitate was filtered off and rinsed thoroughly with petroleum ether. The filtrate was concentrated in vacuo. An oil consisting of crude 2-(2,4-dichlorophenoxy)-1-hydroxy-4,4-dimethyl-pentan-3-one remained.

The compounds of Examples 6 through 22 are produced in a manner analogous to that described in Examples 1 through 5:

| Example No. | Compound |
|---|---|
| (6) | 2,4-Cl₂-C₆H₃-O-CH(CH₂-N(imidazolyl))-CO-C(CH₃)₃ |
| (7) | 4-biphenyl-O-CH(N-imidazolyl)-CH(OH)-C(CH₃)₃ |
| (8) | 4-Cl-C₆H₄-O-CH(CH₂-N(imidazolyl))-CO-C(CH₃)₃ × HCl |
| (9) | 9-(imidazol-1-yl)-9-(2-methylphenyl)fluorene |
| (10) | HC≡C-C(C₆H₅)₂-N(imidazolyl) |
| (11) | (C₆H₅)₂C(COOCH₃)-N(imidazolyl) |
| (12) | 4-biphenyl-O-CH(CH₂-N(imidazolyl))-CO-C(CH₃)₃ |
| (13) | (2-Cl-C₆H₄)(C₆H₅)CH-N(imidazolyl) |
| (14) | (C₂H₅)(C₆H₅)₂C-N(imidazolyl) |
| (15) | (CH₃CO)(C₆H₅)₂C-N(imidazolyl) |
| (16) | (4-Cl-C₆H₄)(C₆H₅)₂C-N(imidazolyl) |
| (17) | (3-Cl-C₆H₄)(C₆H₅)C(N-imidazolyl)₂ |
| (18) | 5-methyl-5-(imidazol-1-yl)-10,11-dihydro-5H-dibenzo[a,d]cycloheptene |
| (19) | 2,4-Cl₂-C₆H₃-O-C(C₆H₅)(N-imidazolyl)-CH(OH)-C(CH₃)₃ |
| (20) | (3-Br-C₆H₄)(C₆H₅)C(N-imidazolyl)₂ |
| (21) | (4-biphenyl)(C₆H₅)C(N-imidazolyl)(N(CH₃)-CH₂-imidazolyl) |

-continued

| Example No. | Compound |
| --- | --- |
| (22) | 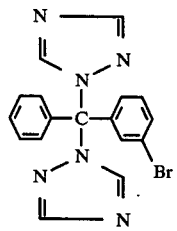 |

What is claimed:

1. A shampoo useful for treating human skin conditions caused by *Pityrosporum ovale* which comprises an amount of a compound of the formula

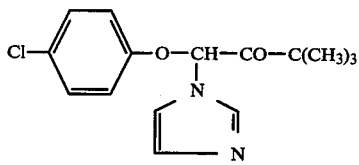

or a physiologically acceptable non-toxic salt thereof sufficient to be effective for the treatment of *Pityrosporum ovale*, in combination with at least 30% by weight of a detergent suitable for use in shampoos which will come in contact with the human skin.

2. A shampoo according to claim 1 wherein the compound is in the form of a physiologically acceptable non-toxic salt.

3. A composition according to claim 1 containing 70% by weight of said detergent.

4. A method of treating humans scalp conditions caused by *Pityrosporum ovale* which comprises applying to the scalp of a human in need thereof an effective amount of a shampoo which comprises an amount of a compound of the formula:

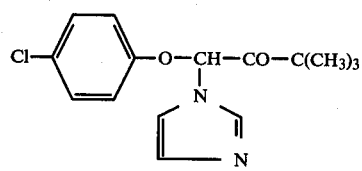

or a physiologically acceptable non-toxic salt thereof sufficient to be effective for the treatment of *Pityrosporum ovale*, in combination with at least 30% by weight of a detergent suitable for use in shampoos which will come in contact with the human skin.

5. A method according to claim 4 wherein the compound is in the form of a physiologically acceptable non-toxic salt.

6. A method according to claim 4 wherein the shampoo contains 70% by weight of said detergent.

* * * * *